United States Patent
Cortes et al.

(10) Patent No.: US 10,589,915 B2
(45) Date of Patent: Mar. 17, 2020

(54) NESTED PACKAGING FOR PHARMACEUTICAL PRODUCTS, AND METHODS OF DISTRIBUTING PHARMACEUTICAL PRODUCTS USING SAME

(71) Applicant: Celgene Corporation, Summit, NJ (US)

(72) Inventors: Edy Cortes, Gland (CH); Thierry Adatte, Delemont (CH)

(73) Assignee: CELGENE CORPORATION, Summit, NJ (US)

( * ) Notice: Subject to any disclaimer, the term of this patent is extended or adjusted under 35 U.S.C. 154(b) by 263 days.

(21) Appl. No.: 15/439,821

(22) Filed: Feb. 22, 2017

(65) Prior Publication Data

US 2017/0240332 A1    Aug. 24, 2017

Related U.S. Application Data

(60) Provisional application No. 62/321,065, filed on Apr. 11, 2016, provisional application No. 62/299,372, filed on Feb. 24, 2016.

(51) Int. Cl.
*B65D 83/04* (2006.01)
*B65D 77/04* (2006.01)
(Continued)

(52) U.S. Cl.
CPC .............. *B65D 77/042* (2013.01); *A61J 1/03* (2013.01); *A61J 1/035* (2013.01); *A61K 31/454* (2013.01);
(Continued)

(58) Field of Classification Search
CPC ............................ B65D 5/4212; B65D 77/042; B65D 77/0433; A61J 1/03; A61J 1/035; A61K 31/454
(Continued)

(56) References Cited

U.S. PATENT DOCUMENTS 1,951,831 A   3/1934 Lewis
2,274,253 A   2/1942 Howell
(Continued)

FOREIGN PATENT DOCUMENTS

DE   20321788 U1   3/2010
FR   1407142 A    7/1965
FR   2864825 A    7/2005

OTHER PUBLICATIONS

MWV: Dosepak® Unit-dose medication packaging [online]. MeadWestvaco Corporation. [retrieved on Oct. 2, 2012]. Retrieved from the Internet: <URL:www.meadwestvaco.com/HealthcarePackagingSoultions/AdherencePackaging/MWV021898>.
(Continued)

*Primary Examiner* — Luan K Bui
(74) *Attorney, Agent, or Firm* — Jones Day (57) ABSTRACT

A pharmaceutical product can be distributed to respective patients in a plurality of jurisdictions. First and second jurisdictions can have different labeling requirements than each other. A plurality of inner containers each store the pharmaceutical product, the pharmaceutical product being in a dosage form and in a package approved by each jurisdiction of the plurality. An inner container can be sealed within a first outer container including labeling required by the first jurisdiction and not required by the second jurisdiction. Another inner container can be sealed within a second outer container including labeling required by the second jurisdiction and not required by the first jurisdiction. The sealed first and second outer containers respectively can be distributed to the first and second jurisdictions.

8 Claims, 6 Drawing Sheets

(51) Int. Cl.
*A61J 1/03* (2006.01)
*A61K 31/454* (2006.01)
*B65B 7/16* (2006.01)
*B65B 43/10* (2006.01)
*B65D 5/02* (2006.01)
*B65D 5/42* (2006.01)
*B65D 77/22* (2006.01)
*B65B 61/20* (2006.01)

(52) U.S. Cl.
CPC .............. *B65B 7/16* (2013.01); *B65B 43/10* (2013.01); *B65D 5/02* (2013.01); *B65D 5/4212* (2013.01); *B65D 77/22* (2013.01); *B65B 61/20* (2013.01); *B65B 2220/16* (2013.01)

(58) Field of Classification Search
USPC ............ 206/232, 528, 534, 459.5, 570, 572; 40/312, 638; 705/330, 336
See application file for complete search history.

(56) References Cited

U.S. PATENT DOCUMENTS

| | | | |
|---|---|---|---|
| 3,204,759 A | 9/1965 | Palmer | |
| 3,240,417 A | 3/1966 | Andreini | |
| 3,349,986 A | 10/1967 | Chapman et al. | |
| 3,437,194 A | 4/1969 | Ames et al. | |
| 3,616,897 A | 11/1971 | Vrana | |
| 3,819,036 A | 6/1974 | Weldon | |
| 4,109,786 A | 8/1978 | Roccaforte et al. | |
| 5,673,796 A | 10/1997 | Tulloch | |
| 5,765,693 A | 6/1998 | Gnadt et al. | |
| 5,775,505 A | 7/1998 | Vasquez et al. | |
| 5,860,526 A | 1/1999 | Burke, Jr. | |
| 6,024,224 A | 2/2000 | Gnadt et al. | |
| 6,789,678 B2 | 9/2004 | Auclair | |
| 7,718,132 B2 | 5/2010 | Thomas et al. | |
| 8,869,984 B2 * | 10/2014 | Bellamah | B65D 83/0463 206/468 |
| 9,051,110 B2 | 6/2015 | Gatto et al. | |
| 2004/0045863 A1 * | 3/2004 | Rhoades | B65D 25/02 206/534 |
| 2005/0150809 A1 * | 7/2005 | Pile | A61J 7/0084 206/570 |
| 2005/0230282 A1 * | 10/2005 | Lapsker | A61J 1/03 206/570 |
| 2009/0050513 A1 * | 2/2009 | Zelek | A01K 13/003 206/534 |
| 2010/0252479 A1 * | 10/2010 | Corroon | A61J 1/03 206/534 |
| 2010/0264058 A1 | 10/2010 | Krause | |
| 2011/0155625 A1 * | 6/2011 | Franks | B65D 23/14 206/534 |
| 2012/0012497 A1 * | 1/2012 | Weston | B65D 83/0463 206/531 |
| 2012/0152796 A1 * | 6/2012 | Leon Alonso | A61J 1/035 206/531 |

OTHER PUBLICATIONS

MWV: Injectapak® Vial/Syringe Packages [online]. MeadWestvaco Corporation, 2012 [retrieved on Oct. 15, 2013]. Retrieved from the internet: <URL:www.meadwestvaco.com/HealthcarePackagingSolutions/InjectableDelivery/MWV021911>.

* cited by examiner

FIG. 4B

NESTED PACKAGING FOR PHARMACEUTICAL PRODUCTS, AND METHODS OF DISTRIBUTING PHARMACEUTICAL PRODUCTS USING SAME

CROSS-REFERENCE TO RELATED APPLICATIONS

This application claims the benefit of the following applications, the entire contents of each of which are incorporated by reference herein:

U.S. Provisional Patent Application No. 62/321,065, filed on Apr. 11, 2016 and entitled "Nested Packaging for Pharmaceutical Products, and Methods of Distributing Pharmaceutical Products Using Same;" and U.S. Provisional Patent Application No. 62/299,372, filed on Feb. 24, 2016 and entitled "Nested Packaging for Pharmaceutical Products, and Methods of Distributing Pharmaceutical Products Using Same."

FIELD

This application relates to packaging for pharmaceutical products, and methods of distributing pharmaceuticals.

BACKGROUND

Different jurisdictions can have different requirements for packaging for pharmaceutical products. Illustratively, different member states within the European Union, such as Austria, Belgium, and Bulgaria, can have requirements for packaging for pharmaceutical products that are the same as one another in some regards, and that are different than one another in other regards. For example, a particular pharmaceutical product can be approved for marketing throughout the European Union, and one or more different pack sizes can be available within each of the member states (e.g., one pack size for a short course of treatment, and one pack size for a monthly course of treatment). As another example, each member state in which a pharmaceutical product is placed on the market can require that the packaging for that product include labeling that is common to all of the member states but that is provided in at least the language(s) of that member state. As another example, some member states of the European Union can require the use of certain forms of labeling in a boxed area (which can be referred to as a "blue box") that should only be presented in the official language(s) of the member state concerned and should state the name of that member state, and with preferably only one such boxed area on the packaging. Illustratively, all member states can require the labeling to require a marketing authorization number, while some member states optionally can require a national identification number that can only appear in the boxed area. Some member states can require specific statements in the boxed area of the legal status of the product, such as "available only in pharmacies," or can require pricing information to be included. Additionally, a leaflet (which also can be referred to as a patient information leaflet) can be included within the packaging and that is presented in at least the language(s) of the member state(s) where the product is placed on the market. Different member states can have different leaflet requirements than one another.

SUMMARY

Embodiments of the presently disclosed subject matter provide nested packaging for pharmaceutical products, and methods of distributing pharmaceutical products using same.

Under one aspect, a method is provided for distributing a pharmaceutical product to respective patients in a plurality of jurisdictions. A first jurisdiction of the plurality can have a different labeling requirement for the pharmaceutical product than a second jurisdiction of the plurality. The method can include providing a plurality of inner containers each storing the pharmaceutical product, the pharmaceutical product being in a dosage form and in a package approved by each jurisdiction of the plurality. The method also can include sealing within a first outer container a first one of the inner containers storing the pharmaceutical product, the first outer container including labeling required by the first jurisdiction and not required by the second jurisdiction. The method also can include sealing within a second outer container a second one of the inner containers storing the pharmaceutical product, the second outer container including labeling required by the second jurisdiction and not required by the first jurisdiction. The method also can include distributing the sealed first outer container to the first jurisdiction; and distributing the sealed second outer container to the second jurisdiction.

Optionally, the dosage form is a pill, tablet, or capsule and the package can include a blister pack.

Additionally, or alternatively, each of the first and second outer containers optionally can include a folding box.

Additionally, or alternatively, the method optionally further can include sealing within the first outer container and outside of the first one of the inner containers a first leaflet approved by the first jurisdiction and not approved by the second jurisdiction; and sealing within the second outer container and outside of the second one of the inner containers a second leaflet approved by the second jurisdiction and not approved by the first jurisdiction.

Additionally, or alternatively, the method optionally further can include sealing the pharmaceutical product within each of the inner containers with a tamper seal.

Additionally, or alternatively, the first one of the inner containers optionally is sealed within the first outer container with a first tamper seal, and the second one of the inner containers optionally is sealed within the second outer container with a second tamper seal.

Additionally, or alternatively, the sealed first outer container optionally is distributed to a retail outlet, wholesale outlet, hospital, pharmacy, or patient in the first jurisdiction, and the sealed second container optionally is distributed to a retail outlet, wholesale outlet, hospital, pharmacy, or patient in the second jurisdiction.

Additionally, or alternatively, the plurality of jurisdictions optionally includes member states of the European Union, the Middle East and North Africa (MENA), or Asia Pacific (APAC) countries.

Additionally, or alternatively, the pharmaceutical product optionally includes pomalidomide, lenalidomide, or other commercial product, such as a future Celgene product.

Under another aspect, packaging is provided for use in distributing a pharmaceutical product to respective patients in a plurality of jurisdictions. A first jurisdiction of the plurality can have a different labeling requirement for the pharmaceutical product than a second jurisdiction of the plurality. The packaging can include a plurality of inner containers each storing the pharmaceutical product, the pharmaceutical product being in a dosage form and in a package approved by each jurisdiction of the plurality. The packaging also can include a first outer container sealing therein a first one of the inner containers storing the pharmaceutical product, the first outer container including labeling required by the first jurisdiction and not required by the second jurisdiction. The packaging also can include a second outer container sealing therein a second one of the inner containers storing the pharmaceutical product, the second outer container including labeling required by the second jurisdiction and not required by the first jurisdiction.

Optionally, the dosage form is a pill, tablet, or capsule and the package can include a blister pack.

Additionally, or alternatively, each of the first and second outer containers optionally can include a folding box.

Additionally, or alternatively, the packaging optionally further can include, sealed within the first outer container and outside of the first one of the inner containers, a first leaflet approved by the first jurisdiction and not approved by the second jurisdiction; and sealed within the second outer container and outside of the second one of the inner containers, a second leaflet approved by the second jurisdiction and not approved by the first jurisdiction.

Additionally, or alternatively, the packaging optionally further can include a tamper seal sealing the pharmaceutical product within each of the inner containers.

Additionally, or alternatively, the first one of the inner containers optionally is sealed within the first outer container with a first tamper seal, and the second one of the inner containers optionally is sealed within the second outer container with a second tamper seal.

Additionally, or alternatively, the plurality of jurisdictions optionally includes member states of the European Union, the Middle East and North Africa (MENA), or Asia Pacific (APAC) countries.

Additionally, or alternatively, the pharmaceutical product optionally includes pomalidomide, lenalidomide, or other commercial products.

Under yet another aspect, a kit is provided for use in distributing a pharmaceutical product to respective patients in a plurality of jurisdictions. A first jurisdiction of the plurality can have a different labeling requirement for the pharmaceutical product than a second jurisdiction of the plurality. The kit can include a plurality of inner containers that are flat and each are foldable into a first shape configured to store the pharmaceutical product, the pharmaceutical product being in a dosage form and in a package approved by each jurisdiction of the plurality. The kit further can include a first outer container that is flat and is foldable into a second shape configured to receive therein a first one of the inner containers storing the pharmaceutical product, the first outer container including labeling required by the first jurisdiction and not required by the second jurisdiction. The kit further can include a second outer container that is flat and is foldable into a third shape configured to receive therein a second one of the inner containers storing the pharmaceutical product, the second outer container including labeling required by the second jurisdiction and not required by the first jurisdiction.

Optionally, the dosage form is a pill, tablet, or capsule and the package can include a blister pack.

Additionally, or alternatively, each of the first and second outer containers optionally includes a folding box.

Additionally, or alternatively, the kit optionally further includes a first leaflet approved by the first jurisdiction and not approved by the second jurisdiction, the first leaflet configured to be sealed within the first outer container and outside of the first one of the inner containers; and a second leaflet approved by the second jurisdiction and not approved by the first jurisdiction, the second leaflet configured to be sealed within the second outer container and outside of the second one of the inner containers.

Additionally, or alternatively, the kit optionally further includes a tamper seal configured to seal the pharmaceutical product within each of the inner containers.

Additionally, or alternatively, the kit optionally further includes a first tamper seal configured to seal the first one of the inner containers within the first outer container with; and a second tamper seal configured to seal the second one of the inner containers within the second outer container.

Additionally, or alternatively, the plurality of jurisdictions optionally includes member states of the European Union, the Middle East and North Africa (MENA), or Asia Pacific (APAC) countries.

Additionally, or alternatively, the pharmaceutical product optionally includes pomalidomide, lenalidomide, or other commercial products.

DETAILED DESCRIPTION

Embodiments of the presently disclosed subject matter provide nested packaging for pharmaceutical products, and methods of distributing pharmaceutical products using same. For example, the present nested packaging can facilitate efficient packaging and distribution of pharmaceutical products without the need for fully customizing the packaging so as to meet the requirements of each individual jurisdiction into which the pharmaceutical product is marketed. Illustratively, the present nested packaging can include an inner container that stores a packaged pharmaceutical product, and that is suitable for distribution to a plurality of jurisdictions. The present nested packaging also can include an outer container into which the inner container can be inserted, and that includes labeling that meets the labeling requirements for only a subset of the jurisdictions. Accordingly, the inner container with packaged pharmaceutical product therein can be mass-produced for distribution to a variety of jurisdictions, while the outer container can include labeling that is customized for one or more of such jurisdictions, thus simplifying and improving the efficiency of manufacture and distribution of the fully packaged product. Methods of distributing pharmaceutical products using nested packaging, and kits including nestable packaging (that is, packaging that can be nested in accordance with embodiments provided herein), also are provided.

Figure 1A:
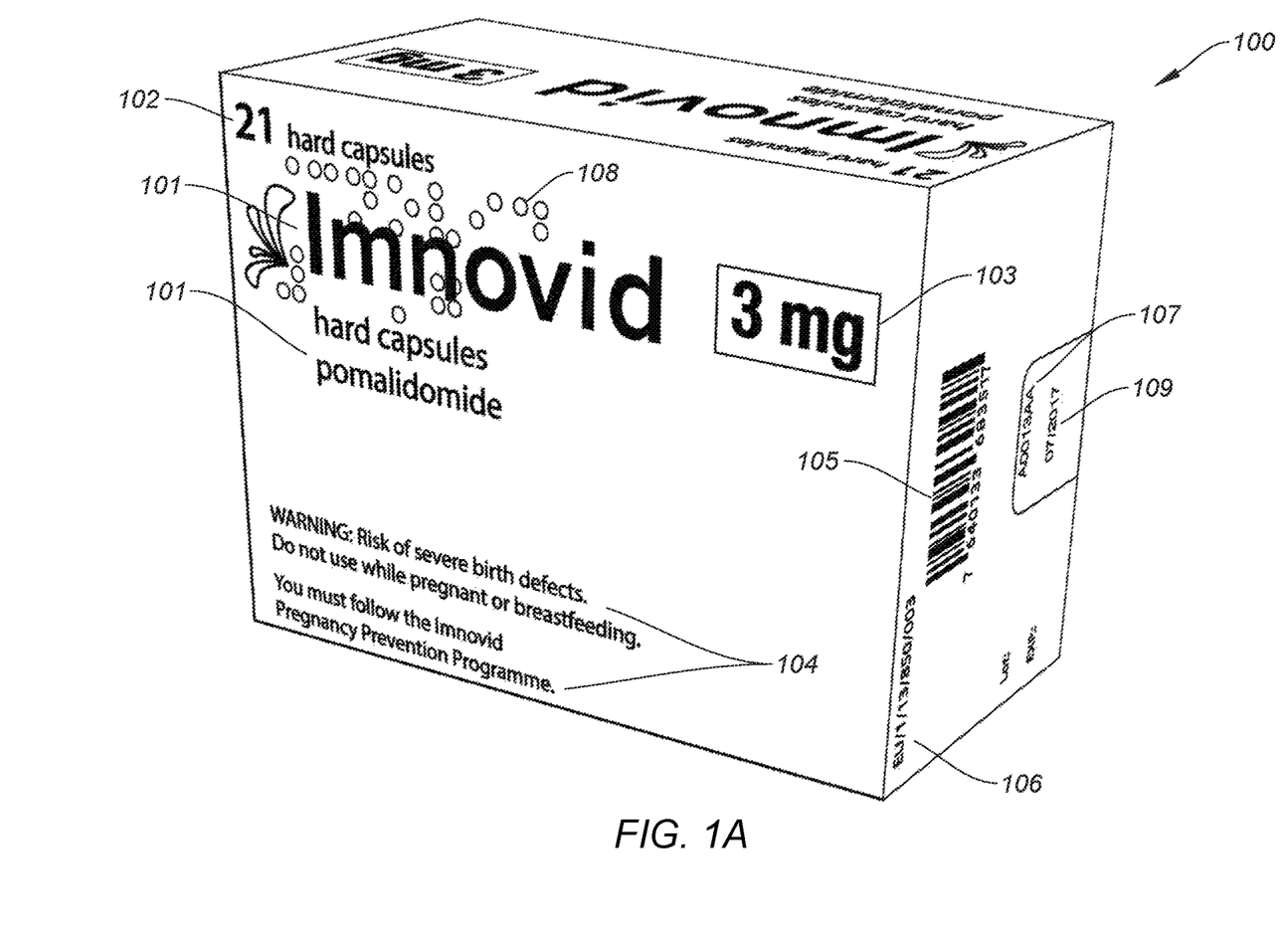
FIGS. 1A and 1B respectively schematically illustrate exemplary inner and outer containers of nested packaging for a pharmaceutical product, according to some embodiments provided herein.
Figure 1B:
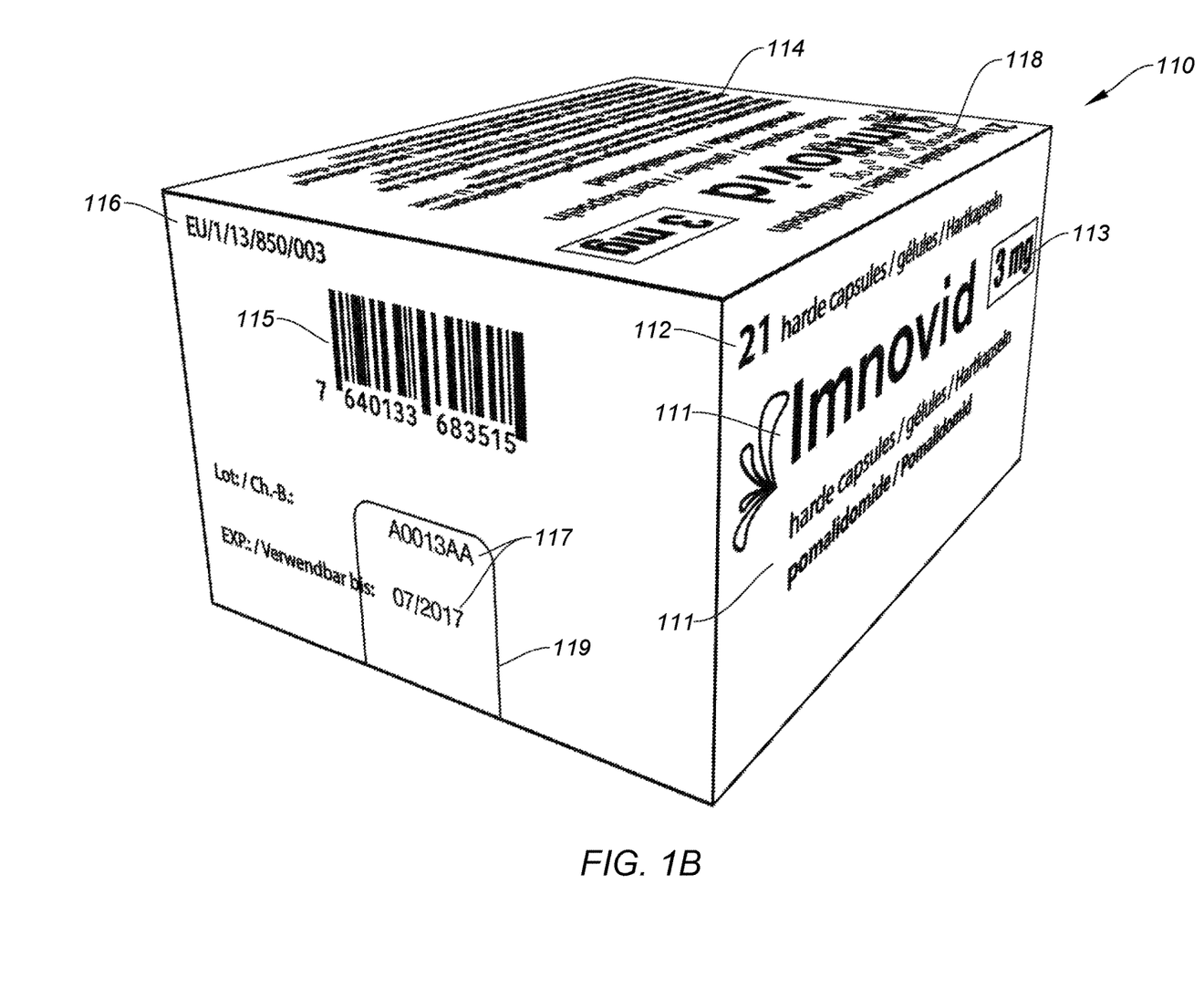

For example, FIGS. 1A and 1B respectively schematically illustrate exemplary inner and outer containers of nested packaging for a pharmaceutical product, according to some embodiments provided herein. The packaging can be for use in distributing a pharmaceutical product to respective patients in a plurality of jurisdictions. A first jurisdiction of the plurality can have a different labeling requirement for the pharmaceutical product than a second jurisdiction of the plurality. For example, as noted above, different member states of the European Union can have some of the same labeling requirements as one another, and also can have some different labeling requirements than one another. Illustratively, the plurality of jurisdictions can include any suitable combination of member states of the European Union, such as any suitable combination of some or all of Austria, Belgium, Bulgaria, Croatia, Republic of Cyprus, Czech Republic, Denmark, Estonia, Finland, France, Germany, Greece, Hungary, Ireland, Italy, Latvia, Lithuania, Luxembourg, Malta, Netherlands, Poland, Portugal, Romania, Slovakia, Slovenia, Spain, Sweden, and the United Kingdom. Additionally, or alternatively, the plurality of jurisdictions can include any suitable combination of countries in the Middle East and North Africa (MENA), such as any suitable combination of some or all of Bahrain, Jordan, Kuwait, Lebanon, Oman, Saudi Arabia, the United Arab Emirates, Algeria, Egypt, Iran, Iraq, Yemen, Libya, Morocco, Palestine, Israel, Qatar, Syria, and Tunesia. Additionally, or alternatively, the plurality of jurisdictions can include any suitable combination of countries in Asia Pacific (APAC) countries, such as any suitable combination of some or all of Brunei Darussalam, Hong Kong, Malaysia, Singapore, South Korea, Thailand, Taiwan, Vietnam, Cambodia, Indonesia, Laos, Myanmar, Philippines, East Timor, China, and Japan.

The present packaging can include a plurality of inner containers each storing the pharmaceutical product. For example, FIG. 1A schematically illustrates a non-limiting example of an inner container 100 of the present packaging. Inner container 100 optionally can include name labeling 101 that identifies one or both of the trade name and generic name of the pharmaceutical product, e.g., IMNOVID® and pomalidomide, respectively, in the non-limiting embodiment illustrated in FIG. 1A. Additionally, or alternatively, inner container 100 optionally can include dosage form labeling 102 that identifies the dosage form, and optionally also the units of dosage form, of the pharmaceutical product, e.g., 21 hard capsules in the non-limiting embodiment illustrated in FIG. 1A. Additionally, or alternatively, inner container 100 optionally can include amount labeling 103 that identifies the amount of pharmaceutical product, such as the amount of each unit dose of the pharmaceutical product, e.g., 3 mg per hard capsule in the non-limiting embodiment illustrated in FIG. 1A, or the total amount of the pharmaceutical product, e.g., in embodiments in which the patient, pharmacist, or hospital may divide the provided amount of the pharmaceutical product into more than one dose.

Additionally, or alternatively, inner container 100 optionally can include one or more warning labels 104 that may advise the patient, pharmacist, or hospital of one or more risks of using the pharmaceutical product or that provides specific usage instructions of which the patient, pharmacist, or hospital should be aware. Additionally, or alternatively, inner container 100 optionally can include one or more bar codes 105 or SKUs (stockkeeping units) that can be used to track the pharmaceutical product during preparation for distribution, e.g., when packaging the pharmaceutical product in the inner container, when shipping the inner container with the pharmaceutical product stored therein, or when packaging into an outer container the inner container with the pharmaceutical product stored therein. Additionally, or alternatively, inner container 100 optionally can include a marketing authorization number 106, e.g., such as one or more jurisdictions may require on any outer packaging for the pharmaceutical product. Additionally, or alternatively, inner container 100 optionally can include variable information 107, such as any suitable combination of one or more of a lot number, a manufacturing date, and an expiration date. Additionally, or alternatively, inner container 100 optionally can include Braille label 108 that provides a portion or all of the information of any of labeling 101, 102, 103, 104, 105, 106, and 107 that may be included on inner container 100. Optionally, any labeling included on inner container 100 (e.g., one or more of labeling 101, 102, 103, 104, 105, 106, 107, and 108) can be provided in any suitable language or languages. However, note that because inner container 100 can be inserted into an outer container such as described further below with reference to FIG. 1B, any jurisdiction-specific labeling requirements for inner container 100 may be significantly reduced, or nonexistent, thus providing the manufacturer with flexibility as to the particular information or labeling (if any) that is provided on inner container 100. For example, any labeling for inner container 100 can be provided in only a single language (e.g., English) or in only a subset of the languages of the jurisdictions to which the packaging ultimately may be sent.

Optionally, the present packaging can include a tamper seal 109 sealing the pharmaceutical product within each of inner containers 100. Such tamper seal 109 can be, but need not necessarily be, in addition to conventional adhesive that can be used to securably store the pharmaceutical product within each of the inner containers. Tamper seal 109 can be configured so as to evidence any attempts to tamper with the contents of inner container 100. Optionally, inner container 100 stores only the pharmaceutical product, and does not store any leaflets. For example, as noted above, different jurisdictions of a plurality of jurisdictions can have different leaflet requirements than one another. As described in greater detail herein, leaflets can be provided within jurisdiction-specific outer packaging, and optionally excluded from the inner packaging, so as to more efficiently meet leaflet requirements that can vary from one jurisdiction to another within a plurality of jurisdictions to which the packaging is to be shipped.

It should be understood that any suitable pharmaceutical product can be packaged within inner container 100. For example, although FIG. 1A illustrates a non-limiting embodiment in which the pharmaceutical product includes pomalidomide (Celgene Corporation, Summit, N.J.), which also is marketed under the trade names IMNOVID® and POMALYST® in various jurisdictions, it should be understood that the invention is not so limited. For example, in another non-limiting embodiment, the pharmaceutical product includes lenalidomide (Celgene Corporation, Summit, N.J.), which also is marketed under the trade name REVLIMID®.

The pharmaceutical product packaged within inner container 100 can be in a dosage form and in a package approved by each jurisdiction of the plurality. For example, as used herein, "pharmaceutical product" is intended to mean a product that is approved in one or more jurisdictions for marketing and distribution to patients for medicinal use in such jurisdiction(s). In various embodiments, the pharmaceutical product can be marketed and distributed to patients in that jurisdiction via any approved method, e.g., can be available on an over-the-counter basis (that is, without prescription), can be available at pharmacies, can be available by mail-order, can be available only by prescription, or can be available at hospitals, or any suitable combination thereof. A pharmaceutical product such as packaged herein can have any suitable dosage form, e.g., can be suitable for oral, mucosal, parenteral (e.g., subcutaneous, intravenous, bolus injection, intramuscular, or intraarterial), topical, transdermal, or transcutaneous administration. Examples of dosage forms include, but are not limited to: pills; tablets; caplets; capsules, such as hard capsules or soft elastic gelatin capsules; cachets; troches; lozenges; dispersions; suppositories; powders; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The composition, shape, and type of dosage forms provided herein will typically vary depending on their use. For example, a dosage form used in the acute treatment of a disease can contain larger amounts of one or more of the active ingredients it comprises than a dosage form used in the chronic treatment of the same disease. Similarly, a parenteral dosage form can contain smaller amounts of one or more of the active ingredients it comprises than an oral dosage form used to treat the same disease. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000). In one specific, nonlimiting embodiment, the dosage form of the pharmaceutical product is a pill, tablet, or capsule and the package comprises a blister pack.

A plurality of outer containers, at least some of which are different than one another, respectively can be used to enclose the inner containers. For example, the present packaging can include a first outer container sealing therein a first one of the inner containers storing the pharmaceutical product, and a second outer container sealing therein a second one of the inner containers storing the pharmaceutical product. The outer container can include labeling required by the first jurisdiction and not required by the second jurisdiction; and the second outer container can include labeling required by the second jurisdiction and not required by the first jurisdiction. For example, FIG. 1B schematically illustrates a non-limiting example of an outer container 110 of the present packaging.

Outer container 110 optionally can include name labeling 111 that identifies one or both of the trade name and generic name of the pharmaceutical product, e.g., IMNOVID® and pomalidomide or Pomalidomid, respectively, in the non-limiting embodiment illustrated in FIG. 1B. Additionally, or alternatively, outer container 110 optionally can include dosage form labeling 112 that identifies the dosage form, and optionally also the units of dosage form, of the pharmaceutical product, e.g., 21 hard capsules in the non-limiting embodiment illustrated in FIG. 1B. Additionally, or alternatively, outer container 110 optionally can include amount labeling 113 that identifies the amount of pharmaceutical product, such as the amount of each unit dose of the pharmaceutical product, e.g., 3 mg per hard capsule in the non-limiting embodiment illustrated in FIG. 1B, or the total amount of the pharmaceutical product, e.g., in embodiments in which the patient, pharmacist, or hospital may divide the provided amount of the pharmaceutical product into more than one dose.

Additionally, or alternatively, outer container 110 optionally can include one or more warning labels 114 that may advise the patient, pharmacist, or hospital of one or more risks of using the pharmaceutical product or that provides specific usage instructions of which the patient, pharmacist, or hospital should be aware. Additionally, or alternatively, outer container 110 optionally can include one or more bar codes 115 or SKUs (stockkeeping units) that can be used to track the pharmaceutical product during preparation for distribution, e.g., when packaging into the outer container the inner container storing the pharmaceutical product, or when shipping the outer container with the inner container therein. Additionally, or alternatively, outer container 110 optionally can include a marketing authorization number 116, e.g., such as one or more jurisdictions may require on any outer packaging for the pharmaceutical product. Additionally, or alternatively, outer container 110 optionally can include variable information 117, such as any suitable combination of one or more of a lot number, a manufacturing date, a 2D barcode, and an expiration date. Additionally, or alternatively, outer container 110 optionally can include Braille label 118 that provides a portion or all of the information of any of labeling 111, 112, 113, 114, 115, 116, and 117 that may be included on outer container 110. Optionally, any labeling included on outer container 110 (e.g., one or more of labeling 111, 112, 113, 114, 115, 116, 117, and 118) can be provided in any suitable language or languages. Note that outer container 110 preferably meets all jurisdiction-specific labeling requirements for outer container 110. For example, any labeling for outer container 110 can be provided in any required languages of the particular jurisdiction to which the packaging ultimately may be sent.

Optionally, the present packaging can include a tamper seal 119 sealing the pharmaceutical product within each of the outer containers. Such tamper seal 119 can be, but need not necessarily be, in addition to conventional adhesive that can be used to securably store each inner container within a selected one of the outer containers. Tamper seal 119 can be configured so as to evidence any attempts to tamper with the contents of outer containers 110. For example, a first one of the inner containers can be sealed within the first outer container with a first tamper seal, and a second one of the inner containers can be sealed within the second outer container with a second tamper seal.

Optionally, each outer container 110 further stores a leaflet. For example, as noted above, different jurisdictions of a plurality of jurisdictions can have different leaflet requirements than one another. Such jurisdiction-specific leaflets can be provided within jurisdiction-specific outer packaging 110, and optionally excluded from the inner packaging, so as to more efficiently meet leaflet requirements that can vary from one jurisdiction to another within a plurality of jurisdictions to which the packaging is to be shipped. For example, the present packaging further can include, sealed within the first outer container and outside of the first one of the inner containers, a first leaflet approved by the first jurisdiction and not approved by the second jurisdiction; and sealed within the second outer container and outside of the second one of the inner containers, a second leaflet approved by the second jurisdiction and not approved by the first jurisdiction.

Note that inner and outer containers 100, 110 independently can respectively include any suitable material(s) in any suitable configuration(s). For example, in the embodiments respectively illustrated in FIGS. 1A and 1B, each of inner and outer containers 100, 110 can include a box, e.g., a folding box (such as a box configured so as to be foldable from a flat, unfolded configuration into a folded configuration), into which the contents of the box can be sealed. The boxes of one or both of inner and outer containers 100, 110 can include cardboard or any other suitable material(s). Illustratively, inner container 100 can be configured so as to fit relatively snugly within outer container 110, e.g., such that inner container 100 can be inserted into outer container 100 relatively easily, e.g., by hand or using robotics, and such that inner container 100 does not move significantly within outer container 110 during transport. In some embodiments, inner container 100 optionally can be fixed within outer container 110, e.g., using glue or another suitable adhesive, so as to inhibit removal of inner container 100 from outer container 110 by the patient or other party. In other embodiments, inner container 100 optionally is removable from outer container 110.

Figure 2:
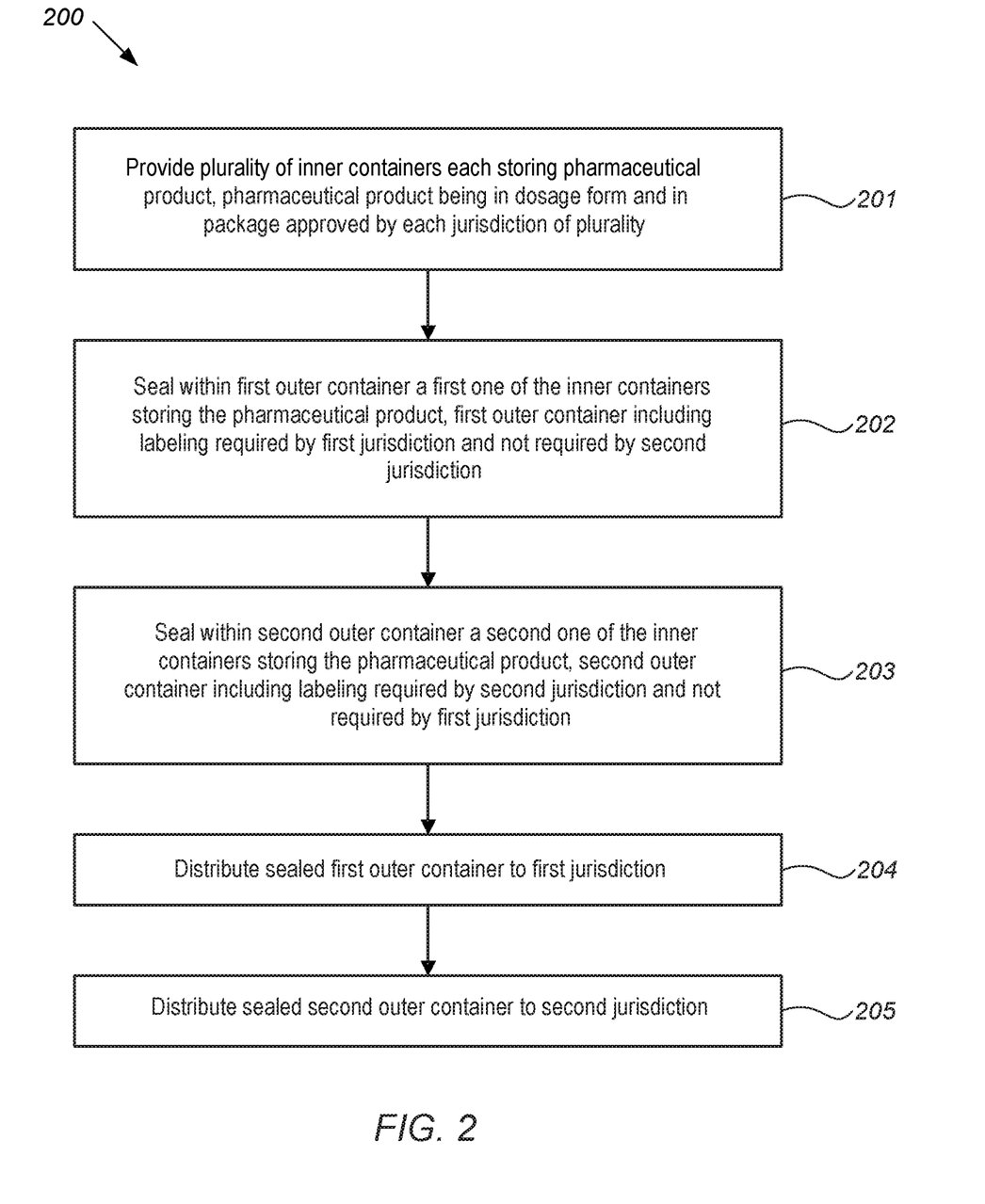
FIG. 2 illustrates a flow of steps in an exemplary method for distributing a pharmaceutical product using nested packaging, according to some embodiments provided herein.

It should be appreciated that nested packaging such as described herein, e.g., with reference to FIGS. 1A-1B, can be used in any suitable distribution method. For example, FIG. 2 illustrates a flow of steps in an exemplary method for distributing a pharmaceutical product using nested packaging, according to some embodiments provided herein. Method 200 can be used for distributing a pharmaceutical product to respective patients in a plurality of jurisdictions, wherein a first jurisdiction of the plurality has a different labeling requirement for the pharmaceutical product than a second jurisdiction of the plurality. Illustratively, the plurality of jurisdictions can include member states of the European Union such as listed above. Additionally, or alternatively, the plurality of jurisdictions can include countries of MENA such as listed above. Additionally, or alternatively, the plurality of jurisdictions can include countries of APAC such as listed above.

Method 200 can include providing a plurality of inner containers each storing the pharmaceutical product, the pharmaceutical product being in a dosage form and in a package approved by each jurisdiction of the plurality (201). For example, step 201 of method 200 can include storing one or more approved packages of an approved dosage form of the pharmaceutical product within an inner container, such as inner container 100 described herein with reference to FIGS. 1A-1B. In one non-limiting example, the dosage form is a pill, tablet, or capsule and the package comprises a blister pack. Illustratively, the pharmaceutical product can include pomalidomide, although it should be appreciated that any other suitable pharmaceutical product can be included. In another nonlimiting example, the pharmaceutical product can include lenalidomide.

Method 200 illustrated in FIG. 2 further can include sealing within a first outer container a first one of the inner containers storing the pharmaceutical product, the first outer container including labeling required by the first jurisdiction and not required by the second jurisdiction (202). For example, step 202 of method 200 can include sealing an inner container, such as inner container 100 described herein with reference to FIGS. 1A-1B, within a first jurisdiction-specific outer container, such as outer container 110 described herein with reference to FIGS. 1A-1B and labeled for a first jurisdiction of the plurality. Optionally, method 200 further can include sealing the pharmaceutical product within each of the inner containers with a tamper seal, e.g., tamper seal 109 such as described herein with reference to FIGS. 1A-1B.

Method 200 illustrated in FIG. 2 further can include sealing within a second outer container a second one of the inner containers storing the pharmaceutical product, the second outer container including labeling required by the second jurisdiction and not required by the first jurisdiction (203). For example, step 203 of method 200 can include sealing an inner container, such as inner container 100 described herein with reference to FIGS. 1A-1B, within a second jurisdiction-specific outer container, such as outer container 110 described herein with reference to FIGS. 1A-1B and labeled for a second jurisdiction of the plurality, wherein the second jurisdiction has at least one labeling requirement that differs from a labeling requirement of the first jurisdiction. In one non-limiting example, each of the first and second outer containers comprises a folding box (such as a box configured so as to be foldable from a flat, unfolded configuration into a folded configuration). Optionally, the first one of the inner containers is sealed within the first outer container with a first tamper seal, and the second one of the inner containers is sealed within the second outer container with a second tamper seal, e.g., tamper seal 119 such as described herein with reference to FIGS. 1A-1B.

Method 200 illustrated in FIG. 2 further can include distributing the sealed first outer container to the first jurisdiction (204); and distributing the sealed second outer container to the second jurisdiction (205). For example, the sealed first outer container can be distributed to a retail outlet, wholesale outlet, hospital, pharmacy, or patient in the first jurisdiction, and the sealed second container can be distributed to a retail outlet, wholesale outlet, hospital, pharmacy, or patient in the second jurisdiction. It should be appreciated that while the outer container of the packaging for the pharmaceutical product can include jurisdiction-specific labeling, the inner container (having the pharmaceutical product stored therein) need not necessarily include any specific labeling, and can be suitable for distribution to any jurisdictions of the plurality when sealed within an appropriately labeled outer container. As such, the inner containers can be produced with high efficiency and in large batches, rather than in smaller batches dedicated to specific jurisdictions, as may otherwise be needed without the use of the jurisdiction-specific outer container.

Optionally, method 200 further can include sealing within the first outer container and outside of the first one of the inner containers a first leaflet approved by the first jurisdiction and not approved by the second jurisdiction; and sealing within the second outer container and outside of the second one of the inner containers a second leaflet approved by the second jurisdiction and not approved by the first jurisdiction. For example, as noted herein, different jurisdictions can have different leaflet requirements.

Figure 3:
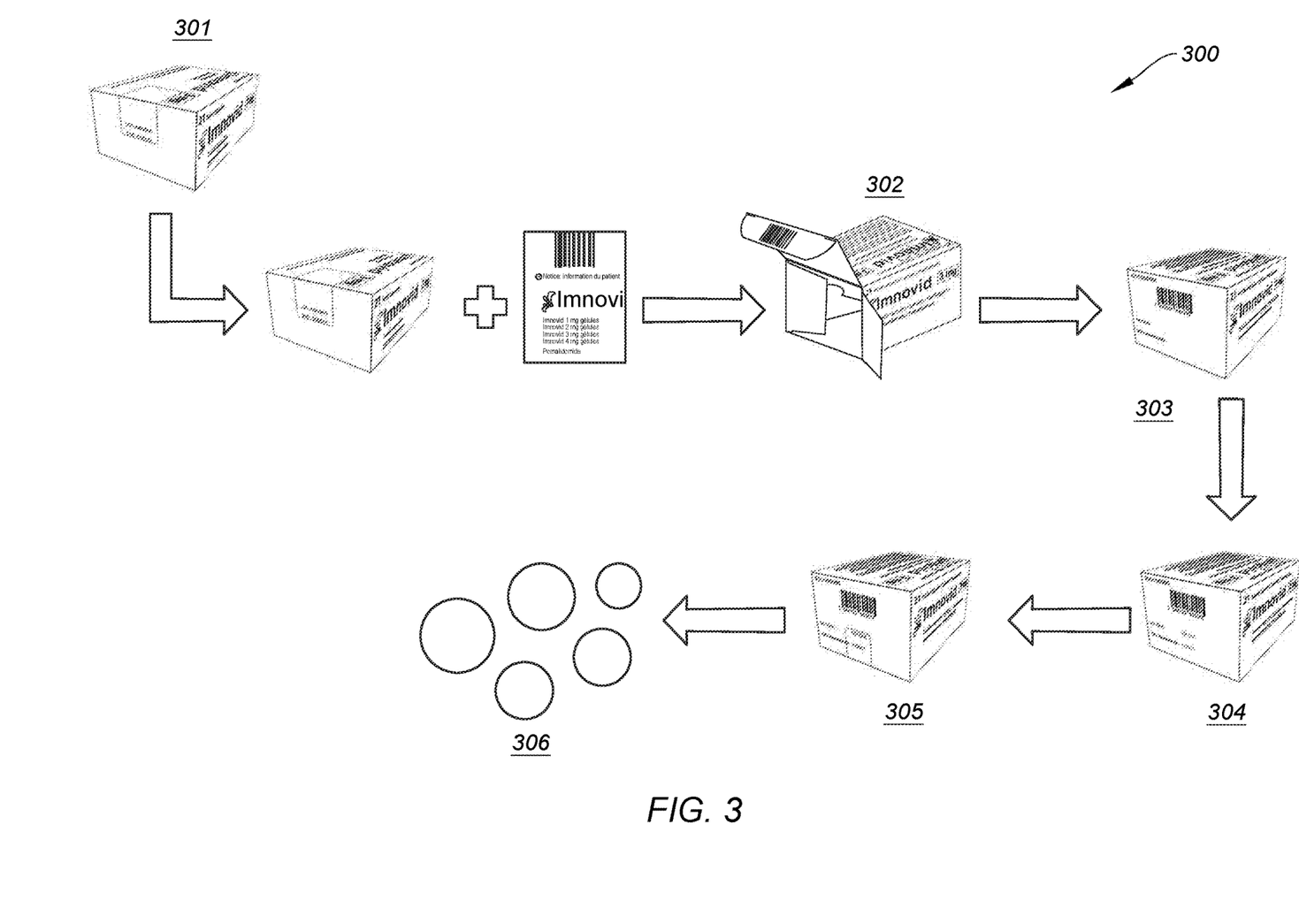
FIG. 3 schematically illustrates a flow of steps in an exemplary method for distributing a pharmaceutical product using nested packaging, according to some embodiments provided herein.

It should be appreciated that the steps of method 200 illustrated in FIG. 2 suitably can be modified or performed in any suitable order. For example, FIG. 3 schematically illustrates a flow of steps in an exemplary method for distributing a pharmaceutical product using nested packaging, according to some embodiments provided herein. Method 300 illustrated in FIG. 3 includes packaging a pharmaceutical product within an inner container by a manufacturer (301). Non-limiting examples of inner containers and pharmaceutical products are provided herein with reference to FIGS. 1A-1B. Optionally, a tamper seal can be used to seal the pharmaceutical product within the inner container, e.g., such as described with reference to FIGS. 1A-1B. The resulting package can be released as a semi-finished product and transported to a distribution center. A jurisdiction-specific outer container can be provided (302). Non-limiting examples of outer containers are provided herein with reference to FIGS. 1A-1B. The inner container, and optionally also a jurisdiction-specific leaflet, can be inserted into the jurisdiction-specific outer container (303) to form a jurisdiction-specific package. Some or all jurisdiction-specific labeling can be applied to the outer container prior to inserting the inner container and optional leaflet into the outer container. Optionally, variable data can be printed on the outer container (304), such as any suitable combination of one or more of a lot number, a manufacturing date, a 2D barcode, and an expiration date, before or after inserting the inner container and optional leaflet into the outer container. A tamper seal optionally can be applied to the outer container (305), e.g., such as described with reference to FIGS. 1A-1B. The jurisdiction-specific outer container(s), having the inner containers, optional leaflets, and pharmaceutical products therein, then can be distributed to respective jurisdiction(s) (306).

Figure 4A:
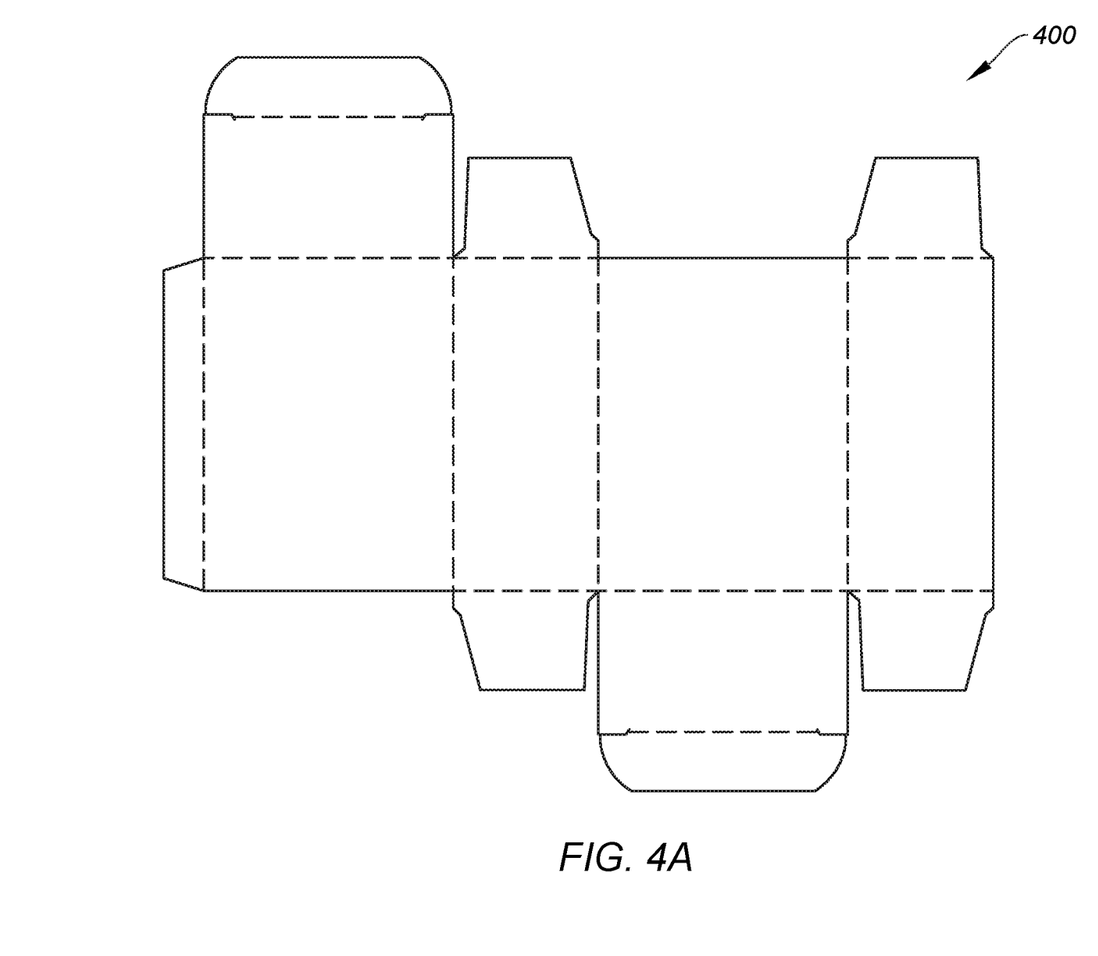
FIGS. 4A-4B respectively schematically illustrate exemplary inner and outer components of a exemplary kit for preparing nested packaging for a pharmaceutical product, according to some embodiments provided herein.
Figure 4B:
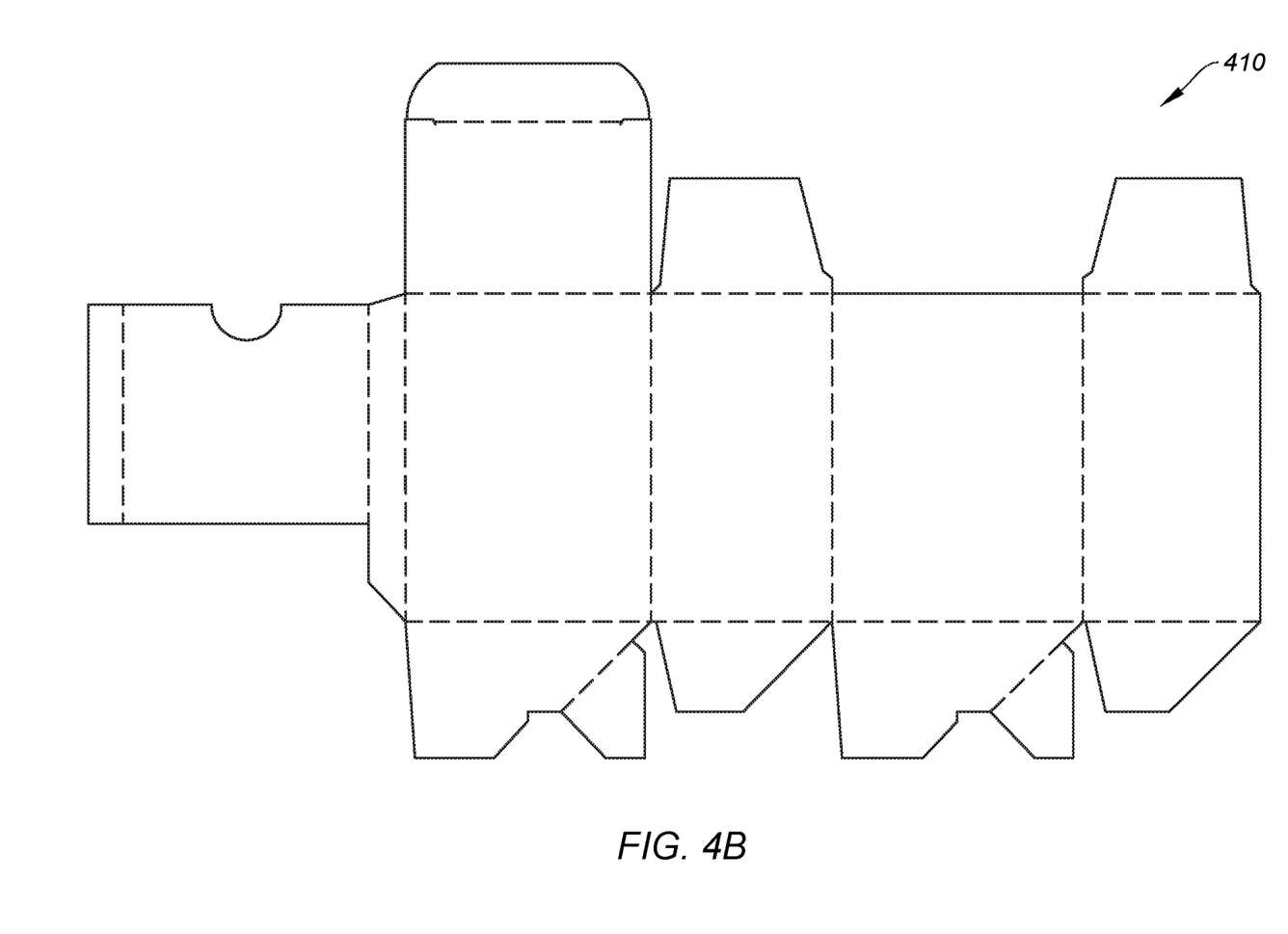

It should be appreciated that the present inner and outer packaging can be provided in any intermediate or finished form. FIGS. 4A-4B respectively schematically illustrate exemplary inner and outer components of a exemplary kit for preparing nested packaging for a pharmaceutical product, according to some embodiments provided herein. The kit can be for use in distributing a pharmaceutical product to respective patients in a plurality of jurisdictions, a first jurisdiction of the plurality having a different labeling requirement for the pharmaceutical product than a second jurisdiction of the plurality. Illustratively, the plurality of jurisdictions can include member states of the European Union such as listed above. Additionally, or alternatively, the plurality of jurisdictions can include countries of MENA such as listed above. Additionally, or alternatively, the plurality of jurisdictions can include countries of APAC such as listed above.

The kit can include a plurality of inner containers that are flat and each are foldable into a first shape configured to store the pharmaceutical product, the pharmaceutical product being in a dosage form and in a package approved by each jurisdiction of the plurality. For example, FIG. 4A illustrates an exemplary inner container 400 that is flat and is foldable into a first shape configured to store the pharmaceutical product. Illustratively, each of the inner containers 400 can be folded into a shape such as discussed herein with reference to FIGS. 1A-1B, e.g., inner container 100. In one non-limiting example, the dosage form can be a pill, tablet, or capsule and the package can include a blister pack. Illustratively, the pharmaceutical product can include pomalidomide. As another example, the pharmaceutical product can include lenalidomide. However, it should be appreciated that any suitable pharmaceutical product can be used.

The kit also can include a first outer container that is flat and is foldable into a second shape configured to receive therein a first one of the inner containers storing the pharmaceutical product, and a second outer container that is flat and is foldable into a third shape configured to receive therein a second one of the inner containers storing the pharmaceutical product. For example, FIG. 4B illustrates an exemplary outer container 410 that is flat and is foldable into a shape that is configured to receive therein an inner container. Illustratively, each of the outer containers 410 can be folded into a shape such as discussed herein with reference to FIGS. 1A-1B, e.g., outer container 110. In one non-limiting example, each of the first and second outer containers 110 comprises a folding box 410 (such as a box configured so as to be foldable from a flat, unfolded configuration such as shown in FIG. 4B into a folded configuration such as shown in FIG. 1B). The first outer container can include labeling required by the first jurisdiction and not required by the second jurisdiction; and the second outer container can include labeling required by the second jurisdiction and not required by the first jurisdiction. Exemplary labeling is described herein with reference to FIGS. 1A-1B.

The kit optionally further can include a first leaflet approved by the first jurisdiction and not approved by the second jurisdiction, the first leaflet configured to be sealed within the first outer container and outside of the first one of the inner containers; and a second leaflet approved by the second jurisdiction and not approved by the first jurisdiction, the second leaflet configured to be sealed within the second outer container and outside of the second one of the inner containers.

The kit optionally can include one or more tamper seals. For example, the kit can include a tamper seal configured to seal the pharmaceutical product within each of the inner containers. Additionally, or alternatively, the kit can include a first tamper seal configured to seal the first one of the inner containers within the first outer container with; and a second tamper seal configured to seal the second one of the inner containers within the second outer container. Exemplary tamper seals 109, 119 are described herein with reference to FIGS. 1A-1B.

While various illustrative embodiments of the invention are described above, it will be apparent to one skilled in the art that various changes and modifications can be made therein without departing from the invention. For example, the present nested packaging suitably can be used to distribute any commercial product to different jurisdictions, and is not limited to use with pharmaceutical products. The appended claims are intended to cover all such changes and modifications that fall within the true spirit and scope of the invention.

What is claimed:

1. Packaging for use in distributing a pharmaceutical product to respective patients in a plurality of jurisdictions, a first jurisdiction of the plurality of jurisdictions having a different labeling requirement for the pharmaceutical product than a second jurisdiction of the plurality of jurisdictions, the packaging comprising:
   the pharmaceutical product;
   a plurality of inner containers each storing the pharmaceutical product, the pharmaceutical product being in a dosage form and in a package approved by each jurisdiction of the plurality of jurisdictions;
   a first one-piece outer container fully enclosing and sealing therein a first one of the plurality of inner containers storing the pharmaceutical product, the first outer container comprising a first label required by the first jurisdiction and not required by the second jurisdiction; and
   a second one-piece outer container fully enclosing and sealing therein a second one of the plurality of inner containers storing the pharmaceutical product, the second outer container comprising a second label required by the second jurisdiction and not required by the first jurisdiction.

2. The packaging of claim 1, wherein the dosage form is a pill, tablet, or capsule and the package comprises a blister pack.

3. The packaging of claim 1, wherein each of the first and second outer containers comprises a folding box.

4. The packaging of claim 1, further comprising:
sealed within the first outer container and outside of the first one of the inner containers a first leaflet approved by the first jurisdiction and not approved by the second jurisdiction; and
sealed within the second outer container and outside of the second one of the inner containers a second leaflet approved by the second jurisdiction and not approved by the first jurisdiction.

5. The packaging of claim 1, further comprising a tamper seal sealing the pharmaceutical product within each of the inner containers.

6. The packaging of claim 1, wherein the first one of the inner containers is sealed within the first outer container with a first tamper seal, and
wherein the second one of the inner containers is sealed within the second outer container with a second tamper seal.

7. The packaging of claim 1, wherein the plurality of jurisdictions comprises member states of the European Union, the Middle East and North Africa, or Asia Pacific countries.

8. The packaging of claim 1, wherein the pharmaceutical product includes pomalidomide, lenalidomide, or other commercial product.

* * * * *